(12) United States Patent
Robson et al.

(10) Patent No.: US 10,744,276 B2
(45) Date of Patent: Aug. 18, 2020

(54) PORTABLE FLUID WARMER

(71) Applicant: FBE Pty Ltd, Bedford Park (AU)

(72) Inventors: John Robson, Bedford Park (AU);
Mark McEwen, Bedford Park (AU);
Robin Woolford, Bedford Park (AU);
David Roxby, Bedford Park (AU)

(73) Assignee: FBE Pty Ltd, Bedford Park (AU)

( * ) Notice: Subject to any disclaimer, the term of this patent is extended or adjusted under 35 U.S.C. 154(b) by 257 days.

(21) Appl. No.: 15/970,663

(22) Filed: May 3, 2018

(65) Prior Publication Data

US 2018/0250478 A1    Sep. 6, 2018

Related U.S. Application Data

(60) Continuation of application No. 15/014,061, filed on Feb. 3, 2016, now Pat. No. 9,962,501, which is a division of application No. 13/881,737, filed as application No. PCT/AU2011/001369 on Oct. 27, 2011, now abandoned.

(30) Foreign Application Priority Data

Oct. 27, 2010    (AU) ................. 2010904779

(51) Int. Cl.
*A61M 5/44* (2006.01)
*F24V 30/00* (2018.01)

(52) U.S. Cl.
CPC .............. *A61M 5/445* (2013.01); *A61M 5/44* (2013.01); *F24V 30/00* (2018.05); *A61M 2205/364* (2013.01)

(58) Field of Classification Search
CPC ........ A61M 5/44; A61M 5/445; A61M 5/364; A61M 2205/364; F24V 30/00; F24J 1/00; A61F 2007/0292; A61F 2007/0293; A61F 2007/0295; C09K 5/18
See application file for complete search history.

(56) References Cited

U.S. PATENT DOCUMENTS 3,171,475 A * 3/1965 Waldman, Jr. .......... A61M 5/44
                                                                  165/67
3,175,558 A    3/1965 Caillonette et al.
(Continued)

FOREIGN PATENT DOCUMENTS

EP    1584343    10/2005
FI    896072    6/1991
(Continued)

OTHER PUBLICATIONS

"Final Office Action", U.S. Appl. No. 13/881,737, dated Feb. 11, 2015, 15 pages.
(Continued)

*Primary Examiner* — Steven S Anderson, II
(74) *Attorney, Agent, or Firm* — Colby Nipper PLLC

(57) ABSTRACT

A warming device, for warming infusion or transfusion fluids by an exothermic reaction of a reactive liquid. The device comprises a reaction chamber and a secondary chamber. The reaction chamber and the secondary chamber are aligned end on and are abutting. The reaction chamber contains a trigger and the secondary chamber contains the reactive liquid.

20 Claims, 5 Drawing Sheets

(56) References Cited

U.S. PATENT DOCUMENTS

| | | | |
|---|---|---|---|
| 4,522,640 A * | 6/1985 | Jagoe, III | A61F 7/106 607/105 |
| 4,530,869 A | 7/1985 | Tesch | |
| 4,576,314 A * | 3/1986 | Elias | B65D 35/32 222/103 |
| 4,723,974 A | 2/1988 | Ammerman | |
| 5,101,804 A * | 4/1992 | Cohn | A61M 5/44 126/263.01 |
| 5,263,929 A * | 11/1993 | Falcone | A61M 5/445 126/263.07 |
| 5,398,850 A | 3/1995 | Sancoff et al. | |
| 5,408,577 A | 4/1995 | Weber et al. | |
| 5,515,558 A | 5/1996 | Dodge | |
| 5,791,334 A * | 8/1998 | Walters | A61F 7/03 126/204 |
| 5,884,812 A | 3/1999 | Stawowski | |
| 6,484,514 B1 | 11/2002 | Joseph et al. | |
| 6,698,504 B2 | 3/2004 | Briesmeister | |
| 7,517,582 B2 | 4/2009 | Amundson et al. | |
| 2003/0124277 A1 * | 7/2003 | Agarwal | A61F 7/02 428/35.2 |
| 2004/0065315 A1 | 4/2004 | Fish et al. | |
| 2005/0224389 A1 | 10/2005 | Azzolini et al. | |
| 2005/0247727 A1 | 11/2005 | Mahurin | |
| 2008/0039815 A1 | 2/2008 | Ogawa | |
| 2008/0245358 A1 | 10/2008 | Bolmer | |
| 2011/0082423 A1 | 4/2011 | Joshi et al. | |
| 2013/0226087 A1 | 8/2013 | King | |
| 2013/0267930 A1 | 10/2013 | Robson et al. | |
| 2014/0066849 A1 | 3/2014 | Ki | |
| 2014/0124187 A1 | 5/2014 | Albalat | |
| 2016/0144136 A1 | 5/2016 | Robson et al. | |

FOREIGN PATENT DOCUMENTS

| | | |
|---|---|---|
| JP | 2009148551 | 7/2009 |
| WO | 9504561 | 2/1995 |
| WO | 2002051482 | 7/2002 |
| WO | 2006056015 | 6/2006 |
| WO | 2008017456 | 2/2008 |
| WO | 2002037037 | 3/2012 |
| WO | 2012054973 | 5/2012 |

OTHER PUBLICATIONS

"Final Office Action", U.S. Appl. No. 13/881,737, dated Nov. 5, 2015, 25 pages.

"Foreign Office Action", JP Application No. 2013-535206, dated Apr. 28, 2015, 4 pages.

"Foreign Office Action", KR Application No. 20137013436, dated Jun. 14, 2017, 7 pages.

"Foreign Office Action", CN Application No. 201180052274.X, dated Jul. 25, 2014, 15 pages.

"Foreign Office Action", JP Application No. 2013-535206, dated Nov. 4, 2015, 2 pages.

"Foreign Office Action", CN Application No. 201180052274.X, dated Nov. 26, 2014, 5 pages.

"International Search Report and Written Opinion", PCT Application No. PCT/AU2011/001369, dated Dec. 6, 2011, 8 pages.

"Non-Final Office Action", U.S. Appl. No. 13/881,737, dated Jun. 4, 2015, 19 pages.

"Non-Final Office Action", U.S. Appl. No. 15/014,061, dated Jul. 26, 2017, 14 pages.

"Non-Final Office Action", U.S. Appl. No. 13/881,737, dated Dec. 2, 2014, 9 pages.

"Notice of Allowance", U.S. Appl. No. 15/014,061, dated Mar. 27, 2018, 8 pages.

"Preliminary Report on Patentability", PCT Application No. PCT/AU2011/001369, dated Apr. 30, 2013, 6 pages.

"Restriction Requirement", U.S. Appl. No. 13/881,737, dated Oct. 2, 2014, 9 pages.

* cited by examiner

PORTABLE FLUID WARMER

CROSS REFERENCE TO RELATED APPLICATION

This application is a continuation of U.S. patent application Ser. No. 15/014,061 filed on Feb. 3, 2016, which is a divisional of U.S. patent application Ser. No. 13/881,737 filed on Apr. 26, 2013, which is a national stage entry of PCT/AU2011/001369 filed Oct. 27, 2011, under the International Convention claiming priority over Australian Patent Application No. 2010904779 filed Oct. 27, 2010.

FIELD OF THE INVENTION

The present invention relates to a compact, self-contained fluid heating device. In particular, the invention relates to devices for heating fluids such as blood that can be used in remote locations.

BACKGROUND OF THE INVENTION

Blood for transfusions is typically stored at approximately 4° C. Prior to patient transfusions, it is preferable that the blood be warmed to a temperature substantially the same as that of the living body, approximately 37° C. Failure to warm the blood prior to transfusion, may result in the patient's core temperature dropping to dangerous levels potentially resulting in hypothermia.

There currently exists a number of portable blood warming devices used in hospitals. These are typically large and cumbersome devices that draw power from a mains supply. In some devices the blood is fed into a spiral tube, which is immersed in a water bath whose temperature is maintained at a set temperature. Other known devices use a heated jacket, which is wrapped around a blood bag, and draw power from the mains supply.

These types of devices, whilst satisfactory in hospital or clinical situations where a constant source of power is available, are not convenient to use in situations that are remote from reliable power sources or in remote locations where it is not practical to carry such large and cumbersome equipment, such as when a patient is moved between wards or geographical locations.

Portable devices for warming blood are also known, such as those devices sold under the THERMAL ANGEL and HOTIV trade marks. Both of these existing devices rely on batteries to provide the source for heating the infusion or transfusion fluid. There are however a number of problems with batteries including that they are heavy, bulky and require replacement or recharging at regular intervals. Given that heating equipment places substantial load on the batteries, it is not possible for these batteries to be small. Additionally, the maintenance issues associated with batteries are such that, for example, if the portable blood warmer is used in an emergency vehicle then it is necessary that regular checks are made on the condition of the battery or indeed that spare batteries are available such that there is always a source of power available. Furthermore, the requirement of batteries in order to operate the blood warmer dramatically increases the overall weight of the apparatus and therefore if rescue workers are required to trek into a remote location this then places an additional burden on them and may complicate matters if the unit fails to operate due to problems associated with the power source. The warming devices can also be used to heat infusion fluids, such as pharmaceuticals and saline fluids.

Portable devices for warming transfusion and infusion fluids using chemical processes to generate the required heat have also been attempted. Disclosures of such attempts can be found in patent documents, U.S. Pat. Nos. 5,042,455, 4,934,336, WO2003059414, WO2008017456, and by the present inventors' earlier application, WO2006056015.

One potential problem of using chemical reaction described in the prior art to generate the required heat, is the challenge of controlling and regulating the heat generated by the chemical reaction, which otherwise has the potential to damage the blood or infusion fluids if the temperature is raised too high. To overcome this problem, the inventors have experimented with using a chemical reaction that releases latent heat, upon solidification, at approximately 42° C., which is about the maximum temperature blood can tolerate before damage may occur. Results of an experiment undertaken by the inventors can be found in the disclosure, McEwen, M. P. and D. Roxby, "Can latent heat safely warm blood?—in vitro testing of a portable prototype blood warmer." BMC Emerg Med, 2007. 7: p. 8.

The inventors have used crystals that react with a chemical liquid to produce the reaction that releases the required latent heat. However a difficulty in using these types of chemical reagents in currently available devices is that the flow of chemical liquid and crystals through the reaction chamber may be too slow. In addition the flow is further hampered by the crystallisation of the reagents that may result in blockages occurring within the reaction chamber. If this occurs the device may not be ideal in an emergency situation where the biological fluid warmer should preferably be fast acting, otherwise particularly in emergency situations the health of the patient may be compromised.

It is thus desirable to have a device for warming blood, or other fluids, that is portable, lightweight, disposable, reliable, economical in cost and manufacture, and that overcomes, or at least substantially ameliorates, the disadvantages and shortcomings of the prior art, or at least provides the public with a choice.

It should be appreciated that any discussion of the prior art throughout the specification is included solely for the purpose of providing a context for the present invention and should in no way be considered as an admission that such prior art was widely known or formed part of the common general knowledge in the field as it existed before the priority date of the application.

SUMMARY OF THE INVENTION

In accordance with an aspect of the invention, but not necessarily the broadest aspect, there is proposed a device for warming infusion or transfusion fluids by an exothermic reaction of a reactive liquid, including at least one reaction chamber containing a trigger, and a passageway extending through said reaction chamber for movement of said infusion or transfusion fluids therethrough, wherein the reactive liquid is introduced into said reaction chamber, being at least partially evacuated of air, to thereby initiate said exothermic reaction.

The reaction chamber may be held at negative atmospheric pressure or alternatively the reaction chamber may be expandable, whereby when expanded the contents of said reaction chamber are at negative atmospheric pressure, for instance the reaction chamber may be collapsible in a concertina type fashion.

The trigger may be a catalyst or another chemical that reacts with said reactive liquid resulting in the crystallisation thereof. In one form the trigger is a chemical trigger, or in another form the trigger is a mechanical trigger.

The trigger for initiating the exothermic reaction may be crystals or alternatively the trigger may be a powder or other particulate that initiates the exothermic reaction.

The passageway extending through said reaction chamber is isolated from the contents of the reaction chamber to inhibit contamination of said infusion or transfusion fluids. The passageway extending through the reaction chamber for movement of the infusion or transfusion fluids therethrough may be a length of flexible tubing.

Preferably the trigger is contained within the reaction chamber and the reactive liquid is contained within a secondary chamber, the reaction and secondary chambers being separated by a frangible or removable barrier.

The reaction and secondary chambers may be flexible wherein the secondary chamber may be compressed to rupture the frangible barrier to thereby introduce the reactive liquid into the reaction chamber.

In another form the barrier is a clamp that separates the reaction and secondary chambers, whereby when the clamp is removed the reactive liquid is able to flow or be compelled into the reaction chamber.

The inventors have discovered that the reaction can be accelerated by introducing the reactive liquid into a reaction chamber that is at least partially evacuated of air, and that contains a trigger such as crystals or particulate matter or any other means that induces the reactive liquid to crystallise. The rapid movement of reactive liquid with respect to the trigger that initialises or promotes crystallization, enables the growing crystals (solidification) to break and spread throughout the reactive liquid without being localized in one part of the reaction chamber that may cause blockages.

In addition, it has been found that a liquid chemical can flow relatively rapidly if there is minimal liquid or gas to displace in the reaction chamber. The rapid flow disrupts, removes or breaks the growing crystals from localising in one area, which would normally be near the inlet port where the reactive liquid first comes into contact with the trigger that initiates the crystallization process and would then normally block or restrict the port. This would then impede or prevent all the reactive liquid from entering the chamber, and thus slowing or preventing a complete chemical reaction from occurring.

The rapid flow of the crystallising liquid chemical can be further enhanced by the avoidance of passing the chemical through narrow openings or large distances. Therefore, in one form the fluid warmer is constructed such that the average distance for the reactive liquid to travel, from all points in the secondary chamber to all points in the reaction chamber will not exceed half the total length of the fluid passageway; and openings of larger than 10 square millimetres are provided for the movement of the chemical within the reaction chamber.

The rapid flow of the crystallising liquid chemical may be yet further enhanced by locating the trigger within the reaction chamber away from both the inlet port and a main liquid chemical pathway or pathways, through the reaction chamber. Keeping these regions free of the trigger can reduce the tendency for crystals to grow in these regions and block or impede the movement of the liquid chemical.

Thus, according to one aspect of the current invention, there is provided a portable, disposable device for warming infusion or transfusion fluids by an exothermic reaction of a reactive liquid, wherein said device includes; a flexible reaction chamber, being at least partially evacuated of air, containing a trigger; a passageway extending through said reaction chamber for movement of said infusion or transfusion fluids therethrough; a flexible secondary chamber containing said reactive liquid, the reaction and secondary chambers being separated by a frangible or removable barrier, wherein the reactive liquid may be introduced into said reaction chamber by rupturing or removing said barrier to thereby initiate said exothermic reaction; and a compression member for forcing said reactive liquid out of said secondary chamber and through said reaction chamber.

Preferably the trigger is held at negative atmospheric pressure within the reaction chamber to assist with the flow of the reactive liquid therethrough.

In one form, when the barrier is removed to start the exothermic reaction, the removal of the barrier causes the reaction and secondary chambers to form one single chamber.

The compression member is used for forcing the reactive liquid into the reaction chamber and past or around the passageway that carries the infusion or transfusion fluid.

The means for forcing the reactive liquid to move may include the manual manipulation of the flexible reaction and/or secondary chambers.

In one form the reaction chamber may be formed within a generally planar envelope constructed from a resiliently flexible material. A portion of said tubing being contained within the envelope, wherein the tubing having an inlet and an outlet extending outwardly from within said envelope, for passage of a fluid therethrough. The envelope is preferably atmospherically sealed such that the reaction chamber is at least partially evacuated of air.

The envelope may be connected to the secondary chamber by way of at least one port and in one form may be connected by a plurality of ports.

A resiliently flexible bladder may form said secondary chamber wherein the compression member may extend along a side of said bladder opposite said port. The compression member in one form is a generally rigid rod, wherein after removal of the barrier between said reaction and secondary chambers the rod may be progressively folded over the bladder, or the secondary chamber may be rolled around the rod, to force the reactive liquid contained therein into the reaction chamber to thereby undergo said exothermic reaction.

The generally empty bladder may be progressively folded over the flexible envelope or the flexible envelope may be rolled around the rod, to move said reactive liquid throughout the reaction chamber. The layering or rolling of the device will reduce the surface area in direct contact with the ambient air and therefore inhibit radiant, convection and conductive heat loss therefrom. Furthermore, the folding or rolling of the device will inhibit crystals from forming a barrier within the reaction chamber that may inhibit movement of the reactive liquid to the extremities of the reaction chamber.

Alternatively the reaction chamber may be formed within a collapsible container or box that in one form includes a foldable frame.

The reactive liquid may be any chemical or mixture of chemicals that produce an exothermic reaction at the desired temperature and with the desired amount of heat energy released.

The reactive liquid chemical may be calcium nitrate tetrahydrate. The trigger for initiating the exothermic reaction may be calcium nitrate tetrahydrate crystals.

The tubing extending through the reaction chamber may be of any suitable configuration that maximises the heat transfer from the exothermic reaction to the infusion or transfusion fluid to be warmed within the tubing.

Preferably, the tubing configuration through the reaction chamber is indirect and in one form is a generally planar serpentine arrangement.

Alternatively, the tubing configuration may be in a spring or coiled arrangement, or may be a layered serpentine arrangement.

The trigger for initiating the exothermic reaction in said reaction chamber may be located in close proximity to the barrier between the reaction and secondary chambers.

The reaction chamber may include a means for aiding in the exothermic reaction or transferral of heat. For instance metal strips may be contained within the reaction chamber for conducting heat to said tube. Furthermore crystals, powder or particulate may be positioned throughout the reaction chamber to assist in a generally constant reaction through the chamber. In one form the crystals, powder or particulate may be attached to the inner wall of reaction chamber, or to the walls of the passageway adjacent the reaction chamber.

In another aspect of the invention there is proposed a device for warming infusion or transfusion fluids by an exothermic reaction of a reactive liquid, including a reaction chamber containing said crystallisation trigger, a secondary chamber containing said reactive liquid, a passageway for movement of the infusion or transfusion fluids therethrough extending through both reaction and secondary chambers such that the portion of the passageway within the reaction chamber being in a compressed state, and a removable barrier between the two chambers, whereby removal of said barrier causes the crystallisation trigger to contact the reactive liquid and permits the compressed passageway to expand, thereby spreading the crystallisation reaction into the reaction chamber.

A further aspect of the invention resides in a method for warming infusion or transfusion fluids to be administered to a patient, the method including the steps of: removing a barrier between a reaction chamber and a secondary chamber of a warming device, the reaction chamber, at least partially evacuated of air, containing a trigger, and the secondary chamber containing a reactive liquid, whereby the removal of the barrier initiates an exothermic reaction of the reactive liquid; and moving said infusion or transfusion fluids through a passageway intersecting said reaction chamber wherein latent heat released by the reactive liquid warms the fluids passing through said passageway.

BRIEF DESCRIPTION OF THE DRAWINGS

The accompanying drawings, which are incorporated in and constitute a part of this specification, illustrate implementations of the invention and, together with the description and claims, serve to explain the advantages and principles of the invention. In the drawings:

DETAILED DESCRIPTION OF THE INVENTION

Figure 1:
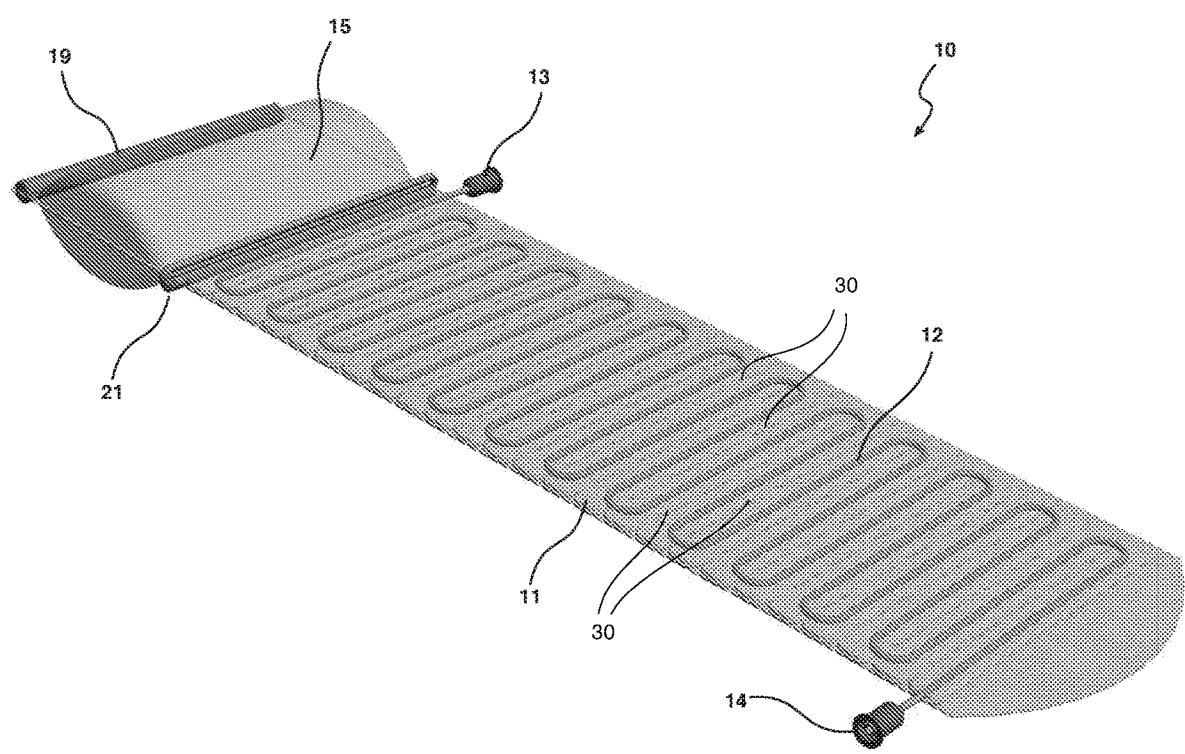
FIG. 1 is a perspective view of a first embodiment of the portable fluid warmer of the present invention.
Figure 2:
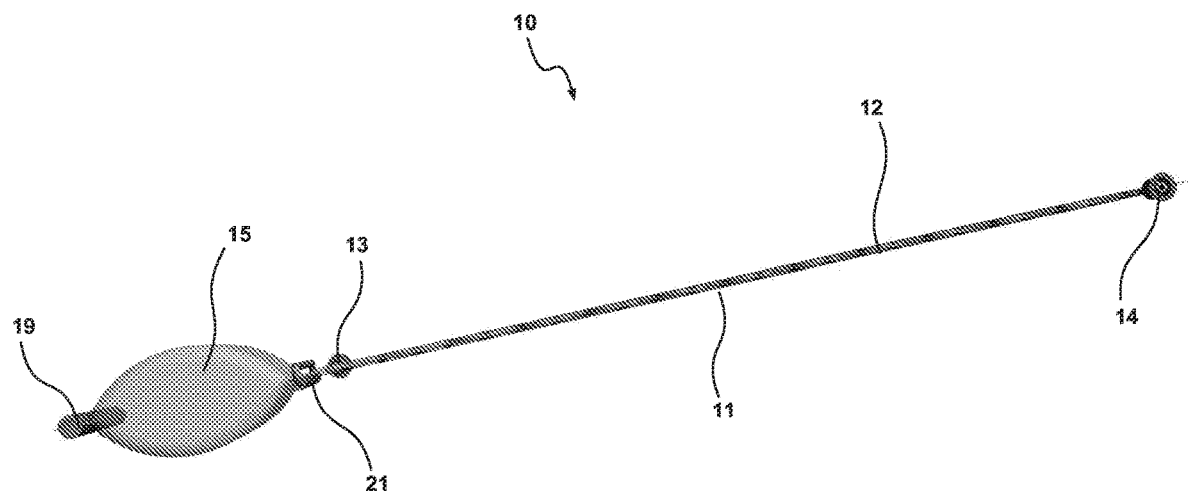
FIG. 2 is side view of the portable fluid warmer of FIG. 1.

Turning to the figures for a detailed explanation of the invention, there is illustrated a fluid heating device demonstrating by way of examples arrangements in which the principles of the present invention may be employed. FIG. 1 illustrates an embodiment of the device (10) of the present invention including a reaction chamber (11) for containing the exothermic reaction. This reaction chamber further contains the tubing (12) in a planar serpentine arrangement through which the infusion or transfusion fluid to be warmed can pass between inlet (14) and outlet (13). As illustrated in FIG. 2 the reaction chamber (11) has a generally envelope shaped configuration. The reaction chamber comprises an upper sheet (11*a*) and a lower sheet (11*b*) there being a plurality of spaced apart connections, some of which are shown at (30) between the upper sheet and lower sheet.

The reaction chamber (11) is connected to a secondary chamber (15) that contains a reactive liquid compound needed for the exothermic reaction. Prior to use the reactive liquid in the secondary chamber (15) cannot enter the reaction chamber because the two chambers are separated by way of a clamp (21), comprising a rigid plastic C section (17) and a flexible rubber insert (18), which acts as a barrier.

Figure 3:
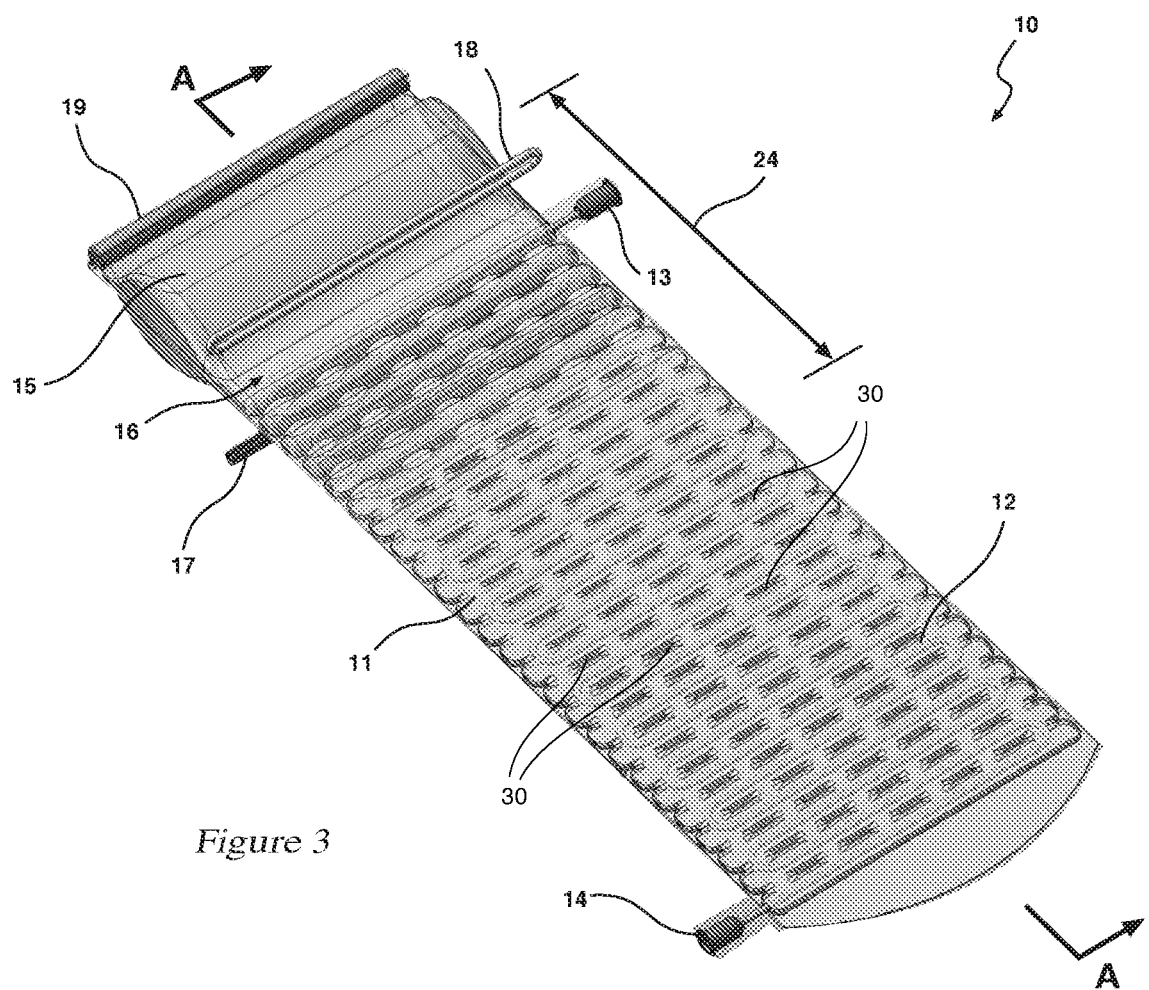
FIG. 3 is a perspective view of the portable fluid warmer of FIG. 1 with the clamp removed.
Figure 4:
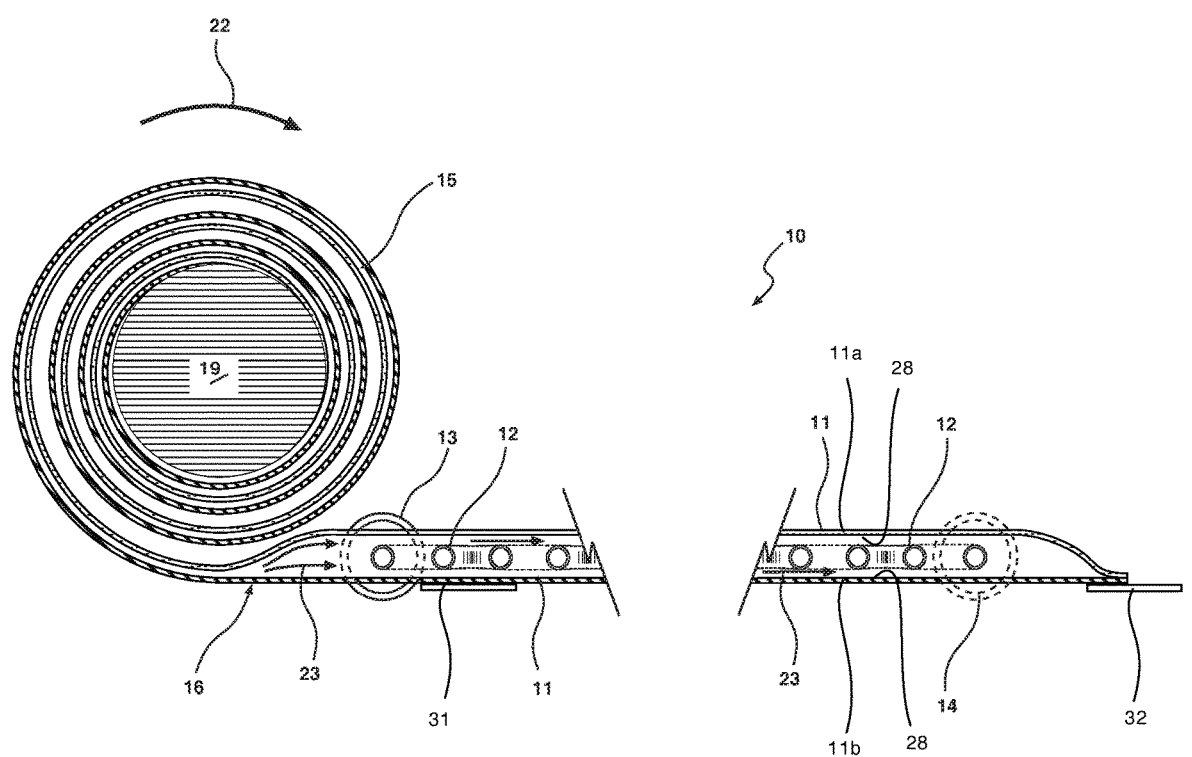
FIG. 4 is a cross sectional view through AA of the portable fluid warmer of FIG. 3 in the process of being rolled.

In use, the rigid plastic C-section (17) and flexible rubber insert (18) are removed, as illustrated in FIG. 3, allowing the reactive liquid to flow through an inlet port (16) into the reaction chamber (11). As the reactive liquid flows into the reaction chamber (11) it will come into contact with the trigger that initiates the exothermic reaction. To ensure a more thorough exothermic reaction throughout the chamber (11) when the clamp (21) has been removed, the secondary chamber (15) can be rolled, in the direction of arrow (22), around a pin (19), as illustrated in FIG. 4, pushing the reactive liquid along the length of the reaction chamber (11), as indicated by arrows 23. The upper sheet (11*a*) and the lower sheet (11*b*) of the reaction chamber are spaced apart approximately parallel to one another constrained by the plurality of connections (30) when the reaction chamber is expanded by the ingress of reactive liquid.

The mechanical action of rolling the chamber improves the mixing of the reactive liquid with the trigger, allowing widespread crystallisation of the reactive liquid and hence faster release of heat to warm the liquid passing through the tubing (12). When the reactive liquid has filled the reaction chamber, the reaction chamber can be rolled around the secondary chamber, to form a compact bundle which can then be secured by a suitable means, such as an adhesive tape or hook and loop fastener (31, 32). The compact layout of the tubing (12) enables the average distance (24) for the reactive liquid to travel, from all points in the secondary chamber (15) to all points in the reaction chamber (11) to be relatively small.

Figure 5:
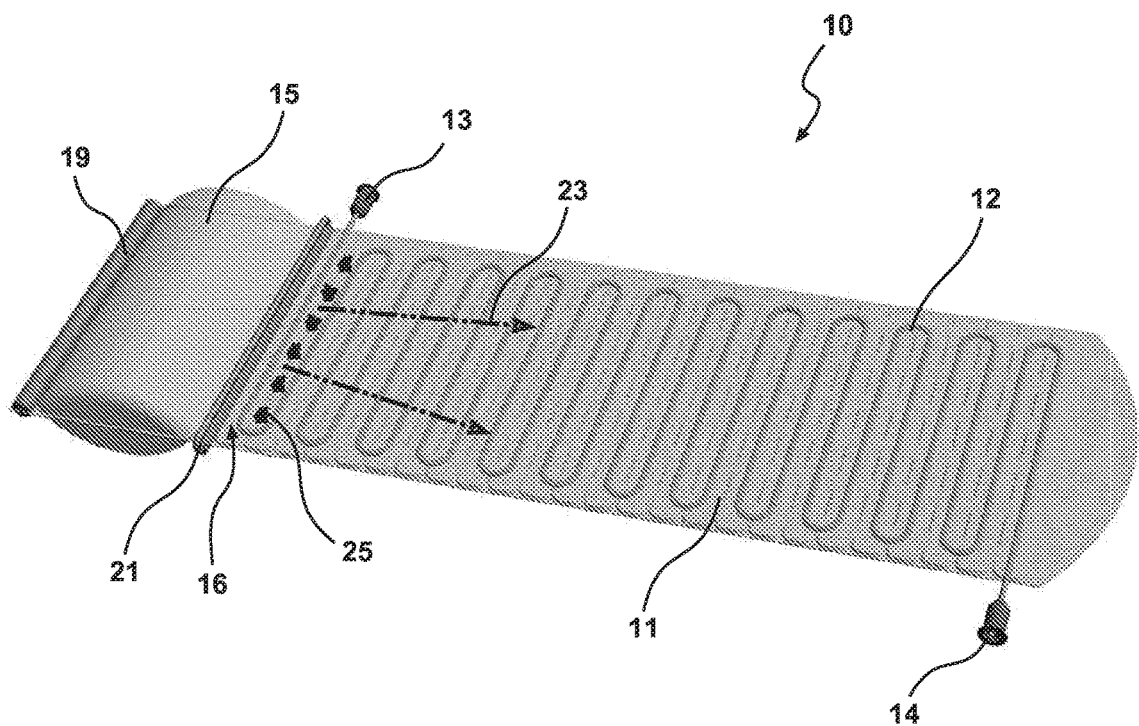
FIG. 5 is a perspective view of the portable fluid warmer of FIG. 1 illustrating the placement of the trigger within the reaction chamber.

The trigger may be crystals (25) that are located adjacent inlet port (16), as illustrated in FIG. 5, such that as the reactive liquid moves past the crystals (25) in the direction of arrows 23 crystallisation is initiated once the clamp (21) has been removed.

Figure 6:
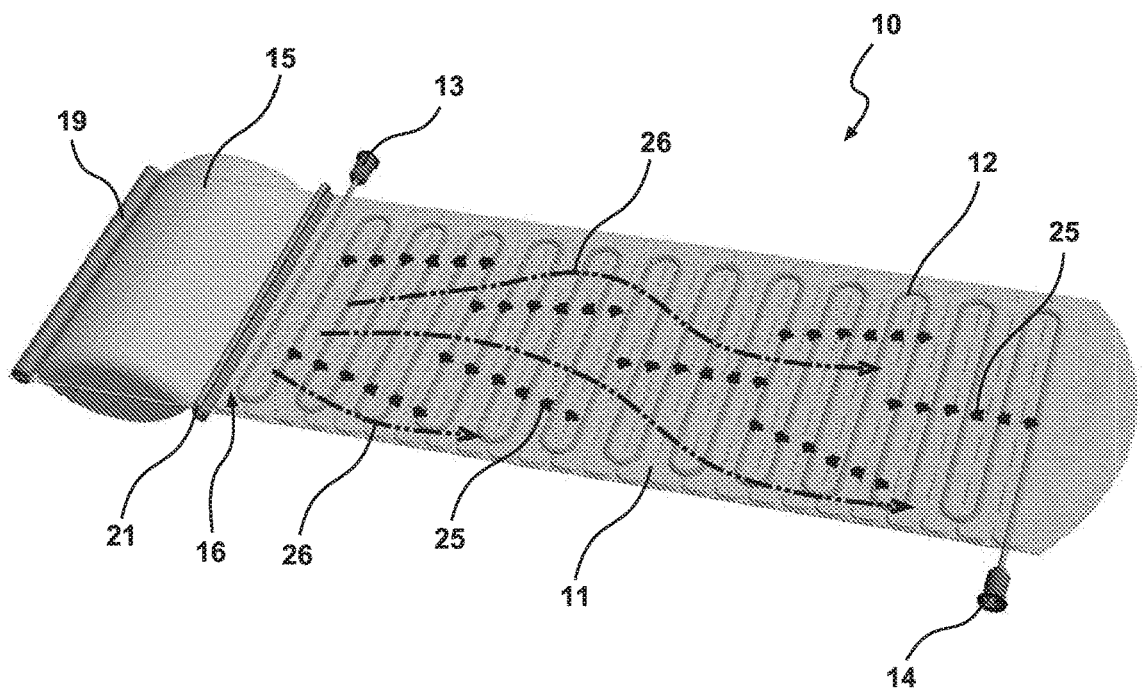
FIG. 6 is a perspective view of the portable fluid warmer of FIG. 1 illustrating an alternate placement of the trigger within the reaction chamber.

The rapid flow of the crystallising liquid chemical may be yet further enhanced by locating the trigger within the reaction chamber away from both the inlet port (16) to thereby create a liquid pathway or pathways (26) through the reaction chamber (11), as illustrated in FIG. 6. Keeping the inlet port (16) free of the trigger can reduce the tendency for crystals to grow and block or impede the movement of the liquid chemical into the chamber, while the provision of pathways (26) controls the crystallisation within the reaction chamber (11).

Accordingly, the above descriptions provide for the use of a fluid warming device that employs relatively inexpensive materials and chemicals that provide for a temperature increase in order to warm the infusion or transfusion fluids in a controlled manner. The low cost and the simplicity of the apparatus make it very suitable for use in emergency situations or in situations where the unit may be stored for a substantial amount of time without having to worry about problems associated with power supply. Since the fluid warming device is lightweight, several may be carried in a field emergency medical kit often used by rescuers travelling to remote locations.

Although the invention has been herein shown and described in what is conceived to be the most practical and preferred embodiment, however, it must be understood that these particular arrangements merely illustrate and that the invention is not limited thereto. Accordingly the invention can include various modifications, which fall within the spirit and scope of the invention.

The invention claimed is:

1. A warming device, for warming infusion or transfusion fluids by an exothermic reaction of a reactive liquid, wherein said warming device comprises:
   a reaction chamber and a secondary chamber;
   the reaction chamber and the secondary chamber are aligned end on and are abutting;
   the reaction chamber containing a trigger;
   the reaction chamber being at least partially empty and unexpanded;
   the secondary chamber containing said reactive liquid;
   the secondary chamber is compressible;
   an inlet port positioned between the secondary chamber and the reaction chamber, the inlet port configured to allow passage of the reactive liquid from the secondary chamber into the reaction chamber to thereby expand the reaction chamber and contact of the reactive liquid with the trigger resulting in exothermic reaction and crystallization of the reactive liquid in the expanded reaction chamber;
   the inlet port being transversely elongate relative to the flow of the reactive liquid;
   the trigger being spaced apart from the inlet port;
   a barrier closing the inlet port;
   tubing extending through the reaction chamber, the tubing extending from a tubing inlet to a tubing outlet, the tubing defining a passageway between the tubing inlet and the tubing outlet, the passageway configured to receive a flow of said infusion or transfusion fluids therethrough; and
   wherein the secondary chamber is configured to be rolled up,
   wherein the reaction chamber is configured to be rolled around the rolled up secondary chamber.

2. The warming device of claim 1, wherein the reaction chamber is planar, comprising an upper sheet and a lower sheet, and comprising a plurality of spaced apart connections there between.

3. The warming device of claim 1, further comprises a compression member, being a rigid rod attached to the secondary chamber distal to the reaction chamber and transverse to the direction of flow of the reactive liquid, wherein the secondary chamber is configured to be compressed by rolling the rigid rod member over the secondary chamber.

4. The warming device of claim 3, wherein the compression member is a rigid rod fastened at an end of the secondary chamber opposite said inlet.

5. The warming device of claim 1, wherein the reaction chamber comprises an upper sheet and a lower sheet, and wherein the trigger is attached to an inner surface of the upper sheet or the lower sheet or both.

6. The warming device of claim 5, wherein the trigger is located throughout the reaction chamber.

7. The warming device of claim 1, in a rolled up form; and a free end of the rolled up reaction chamber secured to an adjacent portion of an outside of the reaction chamber to retain the warming device in a rolled up form.

8. The warming device of claim 1, wherein the barrier comprises at least one of a frangible barrier or a removable barrier.

9. The warming device of claim 1, wherein the tubing, the reaction chamber, and the secondary chamber are flexible.

10. The warming device of claim 2, wherein the upper sheet and lower sheet are spaced apart parallel to one another and constrained by the plurality of spaced apart connections when expanded.

11. The warming device of claim 10, wherein at least one of the upper sheet or the lower sheet are spaced apart from the passageway when expanded.

12. A warming device, for warming infusion or transfusion fluids by an exothermic reaction of a reactive liquid, wherein said warming device comprises:
   a planar reaction chamber and a secondary chamber;
   the reaction chamber and the secondary chamber are aligned end on and are abutting;
   the reaction chamber containing a trigger;
   the reaction chamber comprising:
      an upper sheet;
      a lower sheet spaced apart and parallel to the upper sheet; and
      a plurality of spaced apart connections between the upper sheet and the lower sheet;
   the reaction chamber being at least partially empty and unexpanded;
   the secondary chamber containing said reactive liquid;
   the secondary chamber is compressible;
   an inlet positioned between the secondary chamber and the reaction chamber to allow passage of the reactive liquid from the secondary chamber into the reaction chamber to thereby expand the reaction chamber and contact of the reactive liquid with the trigger resulting in exothermic reaction and crystallization of the reactive liquid in the expanded reaction chamber;
   the inlet being transversely elongate relative to the flow of the reactive liquid;
   the trigger being spaced apart from the inlet;
   a frangible or removable barrier closing the inlet;
   a passageway extending through said reaction chamber, the passageway configured to receive a flow of said infusion or transfusion fluids therethrough; and
   the passageway, the reaction chamber and the secondary chamber all being flexible, so that the secondary chamber can be rolled up,
   wherein the reaction chamber can be rolled around the rolled up secondary chamber,
   wherein the upper sheet and the lower sheet of the reaction chamber are configured to move apart, constrained by the plurality of spaced apart connections, upon ingress of the reactive liquid into the expanded reaction chamber, and wherein at least one of the upper sheet or the lower sheet are spaced apart from the passageway in the expanded reaction chamber.

13. The warming device of claim 12, further comprising:
a compression member, the compression member comprising a rigid rod attached to the secondary chamber distal to the reaction chamber and transverse to the direction of flow of the reactive liquid, wherein the secondary chamber is configured to be compressed by rolling the rigid rod member over the secondary chamber.

14. The warming device of claim 13, wherein the compression member comprises a rigid rod fastened at an end of the secondary chamber opposite said inlet.

15. An apparatus, comprising:
a reaction chamber, the reaction chamber comprising a trigger, the reaction chamber being at least partially empty and unexpanded, the reaction chamber further comprising tubing extending through the reaction chamber from a tubing inlet to a tubing outlet, the tubing defining a passageway between the tubing inlet and the tubing outlet, the passageway configured to receive a flow of fluid therethrough;

a secondary chamber, the secondary chamber containing a reactive liquid, wherein the secondary chamber is compressible;

an inlet port positioned between the secondary chamber and the reaction chamber, the inlet port comprising a barrier closing the inlet port, wherein said barrier is configured for opening, wherein upon barrier opening the inlet port is configured to allow a flow of the reactive liquid from the secondary chamber into the reaction chamber to thereby expand the reaction chamber and contact of the reactive liquid with the trigger resulting in exothermic reaction and crystallization of the reactive liquid in the expanded reaction chamber;

the reaction chamber further comprising the trigger spaced apart from the inlet port; and the secondary chamber configured to be rolled up and the reaction chamber configured to be rolled around the rolled up secondary chamber.

16. The apparatus of claim 15, wherein the tubing, the reaction chamber, and the secondary chamber are flexible.

17. The apparatus of claim 15, wherein the barrier comprises at least one of a frangible barrier or a removable barrier.

18. The apparatus of claim 15, wherein the inlet port is transversely elongate relative to the flow of the reactive liquid.

19. The apparatus of claim 15, wherein the reaction chamber is planar, comprising an upper sheet and a lower sheet, and comprising a plurality of spaced apart connections there between.

20. The apparatus of claim 19, wherein the upper sheet and lower sheet are spaced apart parallel to one another and constrained by the plurality of spaced apart connections when expanded.

* * * * *